(12) United States Patent
Cotticelli et al.

(10) Patent No.: US 6,593,467 B2
(45) Date of Patent: Jul. 15, 2003

(54) PROCESS FOR THE PREPARATION OF A DEOXYURIDINE DERIVATIVE

(75) Inventors: Giovanni Cotticelli, Cernusco sul Naviglio (IT); Giuseppe De Meglio, Milan (IT); Simone Monciardini, Varese (IT); Giancarlo Ordanini, Bedero Valcuvia (IT)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 10/125,351

(22) Filed: Apr. 19, 2002

(65) Prior Publication Data

US 2002/0128467 A1 Sep. 12, 2002

Related U.S. Application Data

(63) Continuation of application No. 09/424,368, filed as application No. PCT/EP98/03171 on May 21, 1998, now abandoned.

(30) Foreign Application Priority Data

May 23, 1997 (IT) .......................... MI97A1211

(51) Int. Cl.[7] .............. C07H 5/04; C07H 5/06; C08B 37/00
(52) U.S. Cl. .................. 536/55.3; 536/28.1; 536/28.55
(58) Field of Search .............................. 536/28.1, 28.55, 536/55.3

(56) References Cited

U.S. PATENT DOCUMENTS

| | | |
|---|---|---|
| 4,071,680 A | 1/1978 | Cook |
| 4,340,729 A | 7/1982 | D'Souza |

OTHER PUBLICATIONS

Ajmera et al, "Synthesis and biological activity of 5'–substituted 5–fluoropyrimidine nucleosides," Journal of Medicinal Chemistry, vol. 25, No. 8, pp. 999–1002 (1982).
Harada et al, "Nucleosides. 139. Synthesis and Anticytomegalovirus and . . . ," Journal of Medical Chemistry, vol. 30, pp. 226–229 (1987).

Primary Examiner—James O. Wilson
Assistant Examiner—Patrick Lewis
(74) Attorney, Agent, or Firm—Nixon & Vanderhye

(57) ABSTRACT

A process for the preparation of 5'-deoxy-5-fluorouridine, which comprises the transformation of 2',3'-O-isopropylidene-5-fluorouridine in the corresponding 5'-O-sulfonyl derivative, subsequent reaction with alkaline or earth-alkaline iodides and, after hydrolysis of the isopropylidene group, reduction of the 5'-deoxy-5'-iodo-5-fluorouridine thus obtained, is described.

19 Claims, No Drawings

PROCESS FOR THE PREPARATION OF A DEOXYURIDINE DERIVATIVE

This application is a continuation of application Ser. No. 09/424,368 filed Mar. 22, 2000, now abandoned, which is a 371 of PCT/EP98/03171 filed May. 21, 1998.

The present invention relates to a process for the preparation of a deoxyuridine derivative. More particularly, the invention concerns a process for the preparation of 5'-deoxy-5-fluorouridine as well as novel intermediates useful in this process.

The compound 5'-deoxy-5-fluorouridine is a well known cytostatic agent which will be hereinafter designated by its International Non-proprietary Name doxifluridine.

Doxifluridine, having the formula I.

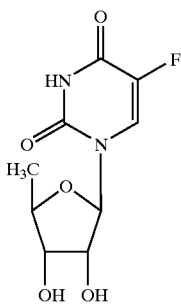

(I)

is described in U.S. Pat. No. 4,071,680, wherein a multi-step synthesis, starting from 5-fluorouridine and involving the removal of the 5'-hydroxy group through the corresponding 5'-iododerivative, is also disclosed. According to this document, the replacement of the 5'-hydroxy group by a iodine atom is accomplished by using triphenylphosphite methoiodide as a chemical iodinating agent which requires a particular caution because of the toxicity of the reagent owing to the presence of reaction by-products.

EP 21,231 discloses the preparation of doxifluridine by removal of the acyl groups from the corresponding 2',3'-diesters with carboxylic acids, particularly from the corresponding 2',3'-diacetate. However, the synthesis of the starting material involves the replacement of an hydroxy group by a bromine atom and the conversion of the bromo derivative into the corresponding deoxy compound by catalytic hydrogenation. In this case too, the bromination is carried out by using a phosphor compound, namely with bromine in the presence of a great amount of triphenylphosphine.

According to a paper by S. Aymera and P. V. Danenberg (J. Med. Chem. 1982, 25, 999) 5'-deoxy-5'-iodo-2', 3'-O-isopropylidene-5-fluoro uridine is prepared according to the method of Cook et al. (J. Med. Chem. 1979, 22, 1330) which corresponds to U.S. Pat. No. 4,071,680. The same paper discloses the conversion of 5'-deoxy-5'-O-mesyloxy-2',3'-O-isopropylidene-5-fluorouridine into 5'-bromo-5'-deoxy-2',3'-O-isopropy lidene-5-fluorouridine by lithium bromide, but it does not describe any further conversion.

On the other hand, in the above cited patent EP 21,231, the replacement of a bromine atom by a hydrogen atom is conducted by catalytic hydrogenation under strong conditions, i.e. in the presence of potassium hydroxide, on a substrate which does not contain the uracil moiety, this one being introduced after the preparation of the deoxy-sugar in the presence of a strong inorganic base.

It has now been found that it is possible to replace the hydroxyl group of 2',3'-isopropylidene-5-fluorouridine by a iodine atom by simply using sodium iodide, in the absence of any phosphor compound, if said hydroxy group is previously activated as a sulfonic ester.

It has also been found that the iodine atom of 5'-deoxy-5'-iodo-2',3'-O-isopropylidene-5-fluorouridine can be replaced by a hydrogen atom by catalytic hydrogenation without using strong bases, thus obtaining the corresponding 5'-deoxy compound in very good yields. The same replacement can take place with other hydrogen donors such as cyclohexene, cyclohexadiene or an hydride, for example tributyltin hydride.

Thus, it is an object of the present invention to provide a process for the preparation of 5'-deoxy-5-fluorouridine, which comprises:

(a) reacting 2',3'-O-isopropylidene-5-fluorouridine to formula II

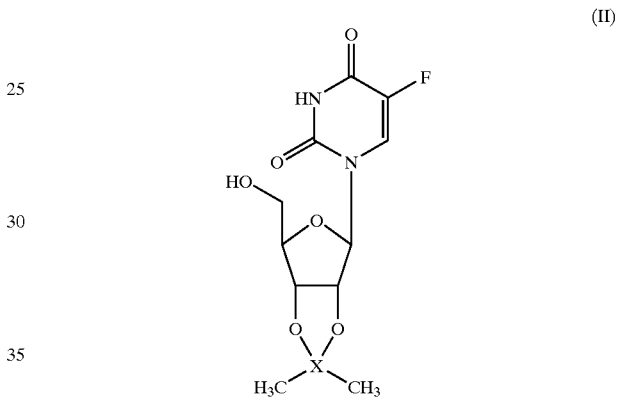

(II)

with a functional derivative of a sulfonic acid of formula III

R—SO₃H (III)

wherein R is a $(C_1-C_4)$alkyl, a trifluoromethyl, an unsubstituted, mono-di- or trisubstituted phenyl group;

(b) reacting the 5'-sulfonyloxy derivative thus obtained of formula IV

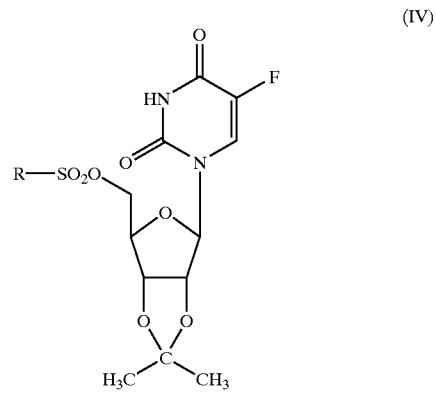

(IV)

wherein R is as defined above, with an alkaline or earth-alkaline iodide;

(c) hydrolysing the 5'-deoxy-5'-iodo-2',3'-O-isopropylidene-5-fluorouridine of formula V

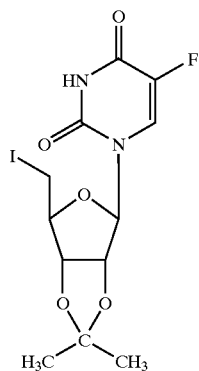

(V)

thus obtained in acidic medium; and (d) submitting the 5'-deoxy-5'-iodo-5-fluorouridine of formula VI

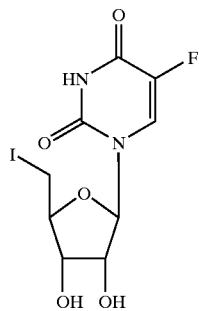

(VI)

to a reduction with hydrogen or a hydrogen donor.

In formula III R is preferably methyl, ethyl, n-butyl, trifluoromethyl, phenyl, monosubstituted phenyl, i.e. with a methyl, methoxy, nitro group or halogen, disubstituted, i.e. with two methyl groups, or trisubstituted, i.e. with three methyl groups, particularly 2,4,6-trisubstituted.

As a functional derivative of the sulfonic acid, the chloride, the anhydride or a mixed anhydride is suitably used. Methanesulfonyl chloride, benzenesulfonyl chloride, p-toluenesulfonyl chloride, trifluoromethanesulfonyl chloride and 2,4,6-trimethylphenylsulfonyl chloride are particularly preferred as esterifying agents.

Thus, in step (a), the functional derivative of the sulfonic acid of formula III, preferably selected from the group consisting of those defined hereinabove, is made to react with 2',3'-O-isopropylidene-5-fluorouridine. Advantageously, the reaction is carried out in an organic solvent, i.e. halogenated such as dichloromethane, 12-dichloroethane or 1,1,1-trichloroethane, or a polar aprotic solvent, such as N,N-dimethylformamide. N,N-dimethylacetamide, dimethyl sulfoxide or acetonitrile, or ethyl acetate or an aromatic hydrocarbon such as toluene or xylene, in the presence of a base such as trimethylamine, triethylamine, diisopropylamine, N-ethyl-diisopropyl amine, pyridine or dimethylaminopyridine.

Generally, after 5÷6 hours at a temperature of 0÷+4020 C., the reaction is complete and the compound of formula IV thus obtained is separated from the reaction by-products by simple filtration of said by-product, after treatment with water.

The 5'-sulfonyloxy derivative of formula IV may be recovered by extraction with an organic solvent, subsequent concentration and may be isolated and characterized according to conventional methods.

Alternatively, the concentrated solution of the compound of formula IV may be straightforwardly used for step (b).

Step (b) is carried out by simply treatment of the compound of formula IV, in pure form or as the said concentrated solution obtained at the end of step (a, with an alkaline or earth-alkaline iodide in an organic solvent such as a ketone, preferably acetone, methylethyl ketone or methylisobutylketone, an ether, preferably dioxane or tetrahydrofurane, or a polar aprotic solvent, preferably acetonitrile, N,N-dimethylformamide, N,N-dimethylacetamide or dimethylsulfoxide.

After 4÷6 hours at a temperature of 40÷80° C., the reaction is complete and, as in the step (a), the by-products of the reaction are removed by filtration and by washing with water. The expected end product, namely 5'-deoxy-5'-iodo-2',3'-O-isopropylidene-5-fluoro uridine of formula V may be recovered with an organic solvent, preferably ethyl acetate, subsequent concentration, and may be isolated according to conventional methods. As in step (a), the concentrated solution containing the compound of formula V may be directly used for step (c).

Step (c) consists of a hydrolysis of 5'-deoxy-5'-iodo-2',3'-O-isopropylidene-5-fluorouridine in acidic medium according to the methods commonly used in the sugar chemistry and, more particularly, in that of the nucleosides. Preferably such an hydrolysis is carried out in aqueous formic acid or, more advantageously, in aqueous acetic acid, or in N,N-dimethylformamide or N,N-dimethylacetamide in the presence of aqueous HCl, at a temperature of 80÷100° C.

The 5'-deoxy-5'-iodo-5-fluorouridine of formula VI thus obtained is isolated by evaporation of the solvent and the compound is recovered by extraction from a suitable solvent, preferably ethyl acetate.

As set Forth hereinabove, the compounds obtained at the end of steps (a) and (b) may be isolated and characterized, or, preferably, they may be used, without isolation, in a raw state or dissolved or suspended in a solvent. The yields of the three steps are very high, namely always higher than 90% of the theoretical and compound of formula VI is recovered in yield as high as 83÷85%, calculated on the starting 2',3'-O-isopropylidene-5-fluorouridine of formula II.

In step (d) the compound of formula VI is subjected to a reduction, which may be carried out by catalytic hydrogenation or by using cyclohexene or cyclohexadiene as hydrogen donors, for example in the presence of Pd/C, preferably at 5%, as a catalyst, or also by a hydride.

The reduction is carried out in an organic solvent, for example in an alcohol, such as methanol, ethanol, propanol, isopropanol or n-butanol or in a mixture thereof. Preferably, an organic base, such as trimethylamine, triethylamine, diisopropylamine, N-ethyldiisopropyl amine, pyridine, dimethylaminopyridine, morpholine, N-methyl morpholine, 2-picoline and quinoline or an inorganic base such as an alkaline bicarbonate, for example sodium bicarbonate or potassium bicarbonate, is present in the reaction mixture.

When the reduction is conducted with hydrogen, the hydrogenation occurs at room pressure or at 1÷2 bar and at room temperature, in the presence of 5% Pd/C.

When the reduction is carried out in the presence of a hydrogen donor, such as cyclohexene, cyclohexadiene or a hydride, for example tributyltin hydride, the reaction takes place in an alcoholic solvent such as methanol, ethanol, isopropanol, n-butanol, isobutanol and the like, or in mixtures of said solvents with an aprotic solvent, such as toluene.

More particularly, when the reduction is conducted with cyclohexene or cyclohexadiene as a hydrogen donor, at a temperature of 60÷9° C., is completed after 3÷6 hours.

The 5'-deoxy-5-fluorouridine thus obtained is isolated according to conventional methods, more particularly by filtering the catalyst and evaporating the solvent. The end product is crystallized with a mixture of ethanol/isopropanol=3/2 (v/v).

When the reduction is carried out by using tributyltin hydride, the reaction takes place by dissolving 5'-deoxy-5'-iodo-5-fluorouridine in an alcohol, for example methanol, the reducing agent being added as a solution in an organic solvent, for example in toluene, and the mixture is heated at reflux in the presence of α,α'-azoisobutyro nitrile in catalytic amount. After 1÷3 hours the reduction is complete and, after evaporation of the solvent, the 5'-deoxy-5-fluorouridine thus obtained is recovered according to conventional methods.

According to a preferred embodiment of the present invention, steps (a), (b) and (c) are carried out without isolating the product obtained at the end of each of steps (a) and (b). Thus, the process of the present invention allows the preparation of doxifluridine in a very easy way and in very high yields. Moreover, this process may be carried out according the one-pot technique as regards steps (a), (b) and (c). Said process is depicted in Scheme I, wherein R is a $(C_1C_4)$alkyl, trifluoromethyl, unsubstitute or mono-, di- or trisubstituted phenyl.

Scheme I

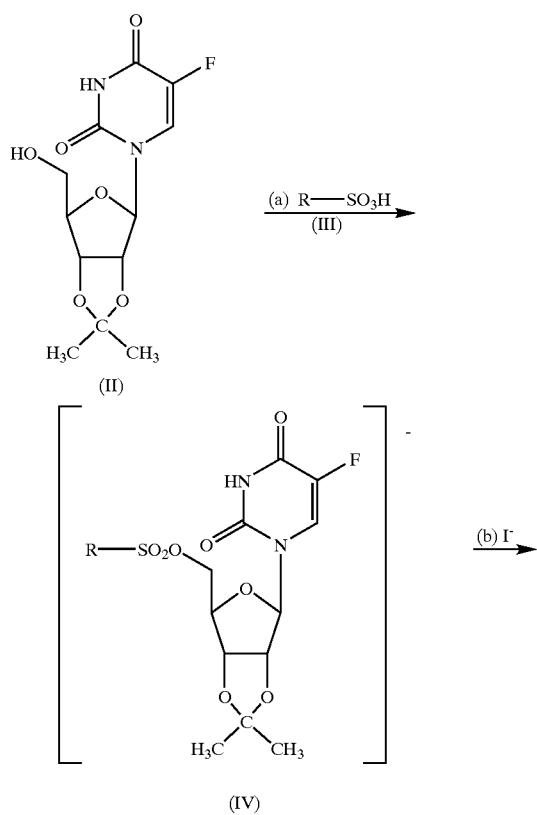

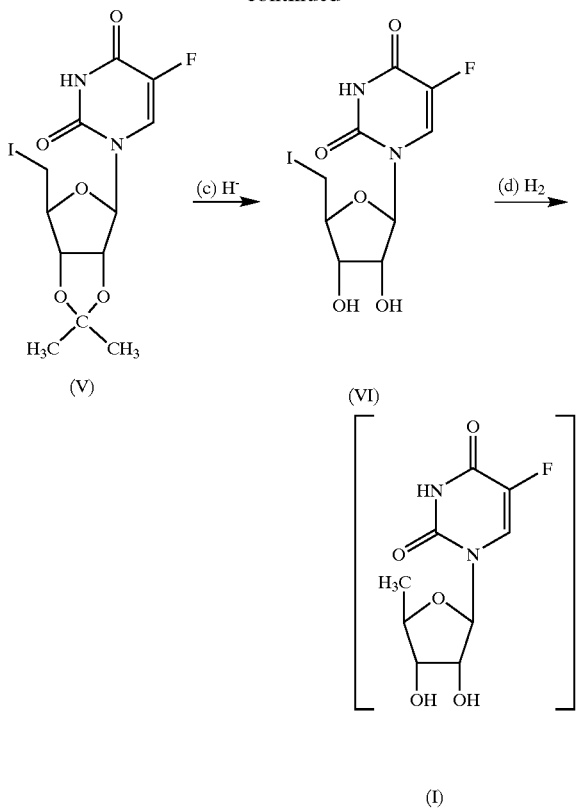

The following examples illustrate the invention without, however, limiting it.

EXAMPLE 1

To a solution of 80 g (0.26 m) of 21',31'-O-isopropylidene-5-fluoro uridine in 700 ml of pyridine, cooled to about +5° C., 90.6 g (0.48 m) of p-toluenesulfonylchloride are added. The mixture thus obtained is stirred for 5 hours, then 10 l of water are slowly added and the aqueous suspension is stirred for 3 hours. The mixture is let to stand at room temperature for 15 hours, then the precipitate is filtered, washed with water and dried. Thus, 99.2 g (83%) of 2',3'-O-isopropyli dene-5'-O-(p-toluenesulfonyl)-5-fluorouridine in crystalline form is obtained. M.p.=154÷156° C.; purity (HPLC)=99.89% and $[\alpha]_D = \div 26,71°$ (c=1, $CH_3OH$).

The product thus obtained may be purified by cystallization with ethanol affording a white crystalline powder. M.p.=156÷158° C.; purity=99.9÷100% (HPLC).

EXAMPLE 2

A. 5'-deoxy-5'-iodo-5-fluorouridine

To a solution of 39.2 g (0.13 m) of 2',3'-O-isopropylidene-5-fluorouridine in 55 ml of methylene chloride and 159 ml (1.98 m) of pyridine, cooled to +5° C., 60 g (0.315 m) of p-toluenesulfonyl chloride are added. The mixture thus obtained is stirred for 5 hours observing the formation of a plentiful precipitate. Then 160 ml of methylene chloride and 160 ml of water are added thereinto, whereby the temperature rises to 40° C. The phases are separated and the organic one is extracted with about 900 ml of N HCl; then the organic phase is washed with 2×100 ml of water. The organic phase, containing 0.117 m of 2',3'-O-isopropylidene-5'-O-(p-toluenesulfonyl)-5-fluorouridine (yield —90% of the theoretical), is concentrated under vacuum until an oily residue is obtained, which is taken up with 2×100 ml of acetone. The oily residue is dissolved with 600 ml of acetone and 105 g (0.70 m) of sodium iodide are added to the solution. The mixture is heated for 5 hours at reflux, then cooled, concentrated under vacuum and the residue thus obtained is taken up with 2×80 ml of ethyl acetate. The residual oil is treated with 800 ml of ethyl acetate and 100 ml of water. The phases are separated and the aqueous one is treated with 2×80 ml of ethyl acetate. The collected organic phases are washed with 2×100 ml of a 5% aqueous solution of sodium metabisulphite, then with 100 ml of water. The organic phase, containing 0.113 m of 5'-deoxy-5'-iodo-2',3'-0-isopropylidene-5-fluoro uridine (yield —97% of the theoretical), is concentrated under vacuum to a small volume; to the residue 560 ml of 80% aqueous acetic acid are added and the mixture is heated to 95° C. After 4-hour heating, a check by HPLC is performed (0.34% of residual starting product) After cooling, the mixture is concentrated under vacuum until an oily residue is obtained, which is taken up with 150 ml of ethyl acetate. The mixture is let to stand at 20÷25° C. for 15 ore. The product is filtered, washed with ethyl acetate and dried under vacuum at 45° C. Thus, 44.5 g of 5'-deoxy-5'-iodo-5-fluorouridine are obtained. M.p.=174÷175° C., purity (HPLC)=99.74% and $[\alpha]_D$=+8.96° C. (c=1, CH$_3$OH). The mother liquors are concentrate under vacuum and the residue is taken up with 50 ml of ethyl acetate; after 15 hours at +5° C., a further amount of 3.3 g of product are obtained. Total yield. 83% of the theoretical.

B. 5'-deoxy-5-fluorouridine

To a suspension of 20 g (0.053 m) of 5'-deoxy-5'-iodo-5-fluoro uridine in a mixture of 60 ml of ethanol and 40 ml of isopropanol, 15.2 ml (0.108 m) of diisopropylamine are added, then 3 g of 5% Pd/C are added thereinto and the mixture is hydrogenated at about 1-bar pressure for 14 hours. After removal of the catalyst by filtration, the solution is concentrated under vacuum until a solid residue is obtained, which is crystallized with a mixture ethanol/isopropanol=60/40 v/v; after 8 hours the product is filtered, washed with said mixture and dried at 45° C. for 15 hours. Thus, 11,6 g (yield—89% of the theoretical) of 5'-deoxy-5-fluorouridine M.p.=187÷188° C., puritya (HPLC)=99,75% and $[\alpha]_D$=+18.2° (c=0.42, H$_2$O).

EXAMPLE 3

To a solution of 40 g (0.087 m) of 2',3'-O-isopropylidene-5'-O-(p-toluenesulfonyl)-5-fluorouridine, obtained as described in Example 1, in 1700 ml of acetone, 105 g of sodium iodide are added and the clear solution thus obtained is heated at reflux for 4+5 hours. Then, the mixture is cooled, filtered and washed wits acetone. The collected acetonic solutions are concentrated under vacuum and the residue is taken up with 3500 ml of ethyl acetate. After washing with 500 ml of 3% aqueous solution of sodium metabisulphite and then with water, the solution in ethyl acetate is concentrated to a small volume. After 15 hours the precipitate is filtered and dried to give 33.2 g of 5'-deoxy -5'-iodo-2',3'-O-isopropylidene-5-fluorouridine as a white crystalline powder. M.p.=199÷202° C., purity (HPLC)=99.9% and $[\alpha]_D$=−16.8° (c=0.50, CH$_3$OH).

EXAMPLE 4

A. 5'-deoxy-5'-iodo-5-fluorouridine

A suspension of 51 g (0.105 m) of 5'-deoxy-5'-iodo-2',3'-O-isopropylidene-5-fluorouridine in 500 ml of acetic acid and 120 ml of water is heated at 95° C. for 90 minutes. The solution thus obtained is concentrated under vacuum and the residue is taken up with 2 l of ethyl acetate, then is concentrated to a small volume and, after 15 hours at room temperature, the precipitate is filtered, washed with ethyl acetate and dried to give 35.6 g of 5'-deoxy-5'-iodo-5-fluoro uridine. M.p.=174.5÷175.5° C., purity (HPLC)=99.74% $[\alpha]_D$=+8.96° (c=1.00, CH$_3$OH).

B. 5'-deoxy-5-fluorouridine

To a solution of 35.1 g (0.07 m) of 5'-deoxy-5'-iodo-5-fluorouridine and 2.93 g of α,α'-azoisobutyronitrile in 1100 ml of methanol, a solution of 37.4 g of tributyltin hydride in 310 ml of toluene is added. The mixture is heated at reflux for 2 hours and the clear solution thus obtained is concentrated under vacuum until a semisolid residue, which is dispersed in 900 ml of petroleum ether. The solid is filtered and treated with 1200 ml of water; the tin salts are separated by filtration and the filtrate is concentrated under vacuum; the residue is crystallized with. 500 ml of hot ethanol to obtain 12.3 g di 5'-deoxy-5-fluorouridine. M.p.=188÷189° C., purity (HPLC)=99.91% and $[\alpha]_D$=+18.4° (c=0.42, H$_2$O).

EXAMPLE 5

To a suspension of 10 g (0.026 m) of 5'-deoxy-5'-iodo-5-fluoro uridine, obtained as described in Example 2, step A, in 100 ml of n-butanol, 6 ml of cyclohexene (0.06 m) and 14 ml (0.1 m) of triethylamine are added. The mixture is heated to 60° C. in order to achieve a complete solubilization, then 1.5 g of 5% Pd/C are added thereinto. The suspension is heated at 80° C. for 5 hours, filtered at the same temperature by washing with hot n-butanol and concentrated under vacuum until a residue is obtained, which crystallizes with a mixture of 60 ml of ethanol and 40 ml of isopropanol. Thus, 4.5 g of 5'-deoxy-5-fluorouridine are obtained. M.p.=188÷189° C., purity (HPLC)=99.87% and $[\alpha]_D$=18.35° (c=0.42, H$_2$O).

What is claimed is:

1. A process for the preparation of 5'-deoxy-5-fluorouridine of formula I

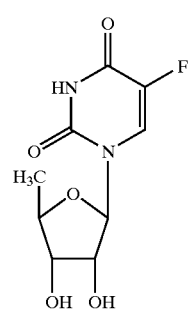

(I)

which comprises:

a) reacting 2',3'-O-isopropylidene-5-fluorouridine of formula II

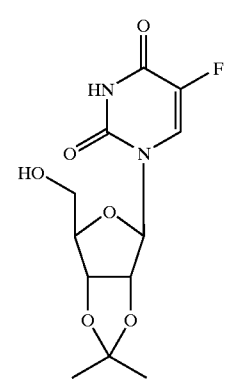

(II)

with a functional derivative of a sulfonic acid of formula III

R—SO₃H    III wherein R is a $(C_1–C_4)$alkyl, a trifluoromethyl, an unsubstituted, mono-di- or trisubstituted phenyl group;

b) reacting the 5'-sulfonyloxyderivative thus obtained of formula IV

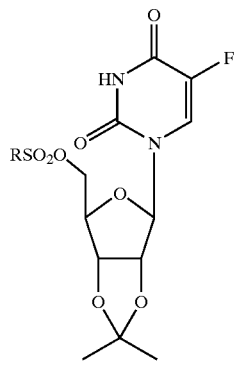

(IV)

wherein R is as defined above, with an alkaline or earth-alkaline iodide;

c) hydrolyzing the 5'-deoxy-5'-iodo-2',3'-O-isopropylidene-5-fluorouridine of formula V

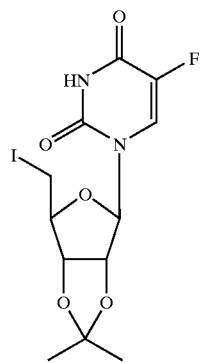

(V)

thus obtained in acidic medium; and d) submitting the 5'-deoxy-5'-iodo-5-fluorouridine of formula VI

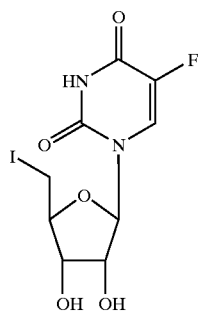

(VI)

to a reduction with hydrogen or a hydrogen donor;

wherein steps (a), (b) and (c) are carried out without isolating the products obtained at the end of each of the steps (a) and (b).

2. A process according to claim 1, wherein in step (a), the choride, the anhydride or a mixed anhydride is used as a functional derivative of the sulfonic acid of formula III.

3. A process according to claim 2, wherein the functional derivative of the acid of formula III is methanesulfonyl chloride, trifluoromethanesulfonyl chloride, benzenesulfonyl chloride, p-toluene sulfonyl chloride or 2,3,4-trimethylphenylsulfonyl chloride.

4. A process according to claim 1, wherein the reduction of step (d) is carried out by catalytic hydrogenation.

5. A process according to claim 4, wherein palladium on charcoal is used as catalyst.

6. A process according to claim 4, wherein said catalytic hydrogenation is carried out in the presence of a base.

7. A process according to claim 6, wherein said base is a secondary or tertiary amine.

8. A process according to claim 7, wherein said secondary or tertiaryamine is trimethylamine, triethylamine, diisopropylamine, N-ethyldiisopropylamine, pyridine, dimethylaminopyridine, morpholinre, N-methylmorpholine, 2-picoline or quinoline.

9. A process according to claim 1, wherein as a reducing agent, tributyltin hydride is used.

10. A process according to claim 9, wherein the reduction is carried out in the presence of α, α'-azoisobutyronitrile, in catalytic amount.

11. A process according to claim 1, wherein the reduction is carried out using cyclohexene or cyclohexadiene as hydrogen donor.

12. A process according to claim 11, wherein said reduction step carried out at a temperature of between 60° C. and 90° C.

13. A process according to claim 1, wherein in said derivative of sulfonic acid of formula III, R is methyl, ethyl, n-butyl, trifluoromethyl, phenyl which may be unsubstituted or monosubstituted by methyl, methoxy, nitro or halogen, disubstituted by two methyl groups or trisubstituted by three methyl groups.

14. A process according to claim 13, wherein said trisubstituted phenyl is 2,4,6 trisubstituted.

15. A process according to claim 6, wherein said base is an inorganic base.

16. A process according to claim 15, wherein said inorganic base is sodium or potassium bicarbonate.

17. A process according to claim 1, wherein said reduction with hydrogen or hydrogen donor is carried out in an alcohol.

18. A process according to claim 17, wherein said alcohol is selected from the group consisting of methanol, ethanol, propanol, isopropanol, n-butanol and mixtures thereof.

19. A process according to claim 8, wherein said base is diisopropylamine.

* * * * *